US009483621B2

United States Patent
Conley et al.

(10) Patent No.: US 9,483,621 B2
(45) Date of Patent: Nov. 1, 2016

(54) AMBULATORY MEDICATION ON DEMAND DISPENSER

(71) Applicant: Avancen MOD Corporation, Melbourne, FL (US)

(72) Inventors: N. Sharon Conley, Ormond Beach, FL (US); Tim Reynolds, Valkaria, FL (US)

(73) Assignee: Advancen MOD Corporation, Melbourne, FL (US)

( * ) Notice: Subject to any disclaimer, the term of this patent is extended or adjusted under 35 U.S.C. 154(b) by 0 days.

(21) Appl. No.: 14/665,122

(22) Filed: Mar. 23, 2015

(65) Prior Publication Data

US 2015/0310186 A1 Oct. 29, 2015

Related U.S. Application Data

(63) Continuation-in-part of application No. 13/080,639, filed on Apr. 5, 2011, now abandoned.

(60) Provisional application No. 61/322,874, filed on Apr. 11, 2010.

(51) Int. Cl.
*G06F 19/00* (2011.01)
*A61J 7/04* (2006.01)

(52) U.S. Cl.
CPC ............ *G06F 19/3462* (2013.01); *A61J 7/049* (2015.05); *A61J 7/0418* (2015.05); *A61J 7/0472* (2013.01)

(58) Field of Classification Search
CPC ....... A61J 7/0472; A61J 7/049; A61J 7/0418
USPC ...................................................... 700/237
See application file for complete search history.

(56) References Cited

U.S. PATENT DOCUMENTS

| 3,367,535 | A | * | 2/1968 | Tanguay | ............ B65D 83/0472 128/203.15 |
|---|---|---|---|---|---|
| 3,410,450 | A | | 11/1968 | Fortenberry | |
| 3,454,194 | A | | 7/1969 | Becker | |
| 4,274,550 | A | | 6/1981 | Feldstein | |
| 4,310,103 | A | | 1/1982 | Reilly | |
| 4,674,652 | A | | 6/1987 | Aten | |
| 4,763,810 | A | | 8/1988 | Christiansen | |
| 5,097,982 | A | | 3/1992 | Kedem | |
| 5,119,969 | A | * | 6/1992 | Haber | ................... A61J 7/0076 221/25 |
| 5,230,441 | A | | 7/1993 | Kaufman | |
| 5,329,459 | A | | 7/1994 | Kaufman | |
| 6,471,087 | B1 | * | 10/2002 | Shusterman | ....... A61B 5/02055 221/2 |
| 6,527,138 | B2 | | 3/2003 | Pawlo | |
| 7,044,302 | B2 | * | 5/2006 | Conley | ................. A61J 7/0472 206/538 |

(Continued)

*Primary Examiner* — Michael K Collins
(74) *Attorney, Agent, or Firm* — John L. DeAngelis; Beusse Woiter Sanks & Maire, PLLC.

(57) ABSTRACT

A medication dispenser. The dispenser comprises a sensor for receiving biometric information from a user, a memory for storing a minimum dosing interval, a controller for determining whether the user is an authorized user, a belt having medication-carrying slots, a dose opening defined in an exterior surface of the dispenser, and a signaling device. The controller activates the signaling device and the sensor only when the minimum dosing interval has elapsed as measured from a last successful user authentication. The sensor is responsive to user biometric information provided any time after activation of the signaling device and the sensor, but not before activation of the signaling device and the sensor. After determining the use is an authorized user, a medication-carrying slot is aligned with the dose opening.

14 Claims, 6 Drawing Sheets

(56) References Cited

U.S. PATENT DOCUMENTS

| | | | |
|---|---|---|---|
| 7,359,765 B2 | 4/2008 | Varvarelis | |
| 7,661,532 B2* | 2/2010 | Conley | A61J 7/0472 206/534 |
| 7,844,362 B2 | 11/2010 | Handfield | |
| 7,896,192 B2* | 3/2011 | Conley | A61J 7/0472 221/15 |
| 8,086,350 B2 | 12/2011 | Timmermans | |
| 8,135,497 B2 | 3/2012 | Joslyn | |
| 8,195,330 B2 | 6/2012 | Coe | |
| 2004/0158349 A1 | 8/2004 | Bonney | |
| 2004/0158350 A1* | 8/2004 | Ostergaard | A61J 7/0481 700/231 |
| 2005/0234430 A1* | 10/2005 | Mao | A61J 7/0481 604/890.1 |
| 2008/0119958 A1 | 5/2008 | Bear | |
| 2008/0283542 A1 | 11/2008 | Lanka | |
| 2008/0300719 A1 | 12/2008 | Duke | |
| 2009/0281657 A1 | 11/2009 | Gak et al. | |
| 2010/0305749 A1 | 12/2010 | Coe | |
| 2011/0022224 A1 | 1/2011 | Park | |
| 2011/0270442 A1* | 11/2011 | Conley | G06F 19/3462 700/237 |
| 2015/0310186 A1* | 10/2015 | Conley | G06F 19/3462 700/237 |

* cited by examiner

AMBULATORY MEDICATION ON DEMAND DISPENSER

The present invention is a continuation-in-part of the application filed on Apr. 5, 2011 and assigned application Ser. No. 13/080,639, which claims priority, under 35 U.S.C. 119(e) to the provisional patent application filed on Apr. 11, 2010 and assigned application No. 61/322,874.

FIELD OF THE INVENTION

The present invention relates generally to a medication dispenser, and more particularly to an ambulatory time-controlled medication on-demand dispenser.

BACKGROUND OF THE INVENTION

It is generally agreed that there are two concurrent public health crises in the United States: under-treated pain and prescription drug abuse. Although the United States represents only 4% of the world's population, we consume 80% of the global supply of opioids and two-thirds of the world's illegal drugs. Our rising use of prescription opioids for legitimate pain is mirrored by a rising abuse of prescription drugs, in addition to known "street drugs," and consensus statements agree that the need for substance abuse and addiction therapy in the US is rising and that "treatment as usual" will not be able to meet the demands of the 21st century. It will therefore be necessary to create and adopt new ideas and technologies to reach more patients for improved, or at least equivalent, effective therapy.

Although drug abuse therapy saves lives and healthcare dollars, only a small portion of addicted individuals are enrolled in treatment programs. In 2008, 23 million persons age 12 or older were classified as needing substance abuse treatment although only 10% received treatment at a specialty facility.

Multiple factors contribute to this inequity in treatment—including limited availability of clinical services, difficulty recruiting service providers, limited financing for services and an increasing need in rural communities, where services are most limited. Of course it is well known that many substance abusers refuse therapy, but this does not negate the fact that not enough treatment facilities exist for those who seek therapy.

Most patients are treated in outpatient certification-based opioid treatment programs (OTPs) overseen by various federal agencies. Qualified physicians can also provide opioid addiction therapy in their offices outside OTP clinics, provided they have received specialized training. However, very few physicians have opted to participate in this program and one key reason has been the inability to provide a program of education and counseling services that should be part of an effective therapy.

The principles of drug abuse therapy rely on an induction treatment phase to replace the abused opioid with an opioid agonist or partial agonist to prevent withdrawal symptoms from discontinued illicit drug(s). Most commonly, methadone is used in OTP programs and either buprenorphine (Subutex) or buprenorphine/naloxone (Suboxone) are the preferred treatment regimen for in-office treatment. Following the induction dose, patients can remain on an opioid maintenance dose with careful clinic observation until stabilization occurs with regard to drug craving and abuse with outside opioids or psychogenic drugs. Compliance is documented by frequent urine screening to validate that patients are not taking additional outside illicit drugs. Patient alcohol consumption is also monitored. Patients may ultimately transition to less frequent outpatient follow-up and remain on maintenance therapy or attempt total withdrawal from opioids with careful management and supervision.

Successful treatment programs combine opioid substitution therapy with counseling and addiction recovery programs. Research has shown that behavioral therapies, including cognitive behavior therapy, contingency management, couples and family therapy, and other similar treatments contribute to better long-term outcomes in these programs.

The length of patient retention in a treatment program is the most important indicator of treatment outcome. Recommendations to improve retention include:
  individualized medication dosing;
  clear program goals;
  a clear treatment plan for the patient;
  enhanced staff-/patient interactions; and
  a reduction in the attendance burden for the patient.
Positive incentives (contingency management) and rewards for treatment compliance have a motivating effect on continued therapy. One of the most effective rewards is granting medication take-home privileges to a patient.

The burden of frequent travel to a therapy clinic also influences clinic retention rates. This may be particularly problematic in rural areas or in cases where transportation is difficult to arrange.

BRIEF DESCRIPTION OF THE DRAWINGS

The various features of the invention will be apparent from the following more particular description of the invention, as illustrated in the accompanying drawings, in which like reference characters refer to the same parts throughout the different figures. The drawings are not necessarily to scale, emphasis instead being placed upon illustrating the principles of the invention.

DESCRIPTION OF THE INVENTION

Before describing in detail the particular method and apparatus related to an ambulatory medication-on-demand dispenser, it should be observed that the present invention resides primarily in a novel and non-obvious combination of elements and process steps. So as not to obscure the disclosure with details that will be readily apparent to those skilled in the art, certain conventional elements and steps have been presented with lesser detail, while the drawings and the specification describe in greater detail other elements and steps pertinent to understanding the invention.

The following embodiments are not intended to define limits of the structure or method of the invention, but only to provide exemplary constructions. The embodiments are permissive rather than mandatory and illustrative rather than exhaustive.

The ambulatory medication on demand dispenser (referred to commercially as an A-MOD) of the present invention is a unique and non-obvious secure handheld device for safely dispensing oral opioids, any psychotherapeutic drug with abuse potential, or other medications. The device can be activated only by the person for whom the medication was prescribed and within the prescribed dosing and dosing timing parameters. That is, a medication dose is presented to the patient/user only after the minimum dosing interval has elapsed, after the patient/user has been successfully authenticated, and after the patient/user has rotated a knob that moves a dose-carrying belt (or the belt has been automatically moved) to present a dose at a dose portal or opening. The A-MOD dispenser can be used in a variety of applications for different patient groups, i.e., pain patients taking opioids, substance abuse patients taking opioids, palliative care and hospice patients taking opioids, physical rehabilitation patients after surgery and school age children taking psychotherapeutic medications during the school day. The invention can also be used in pharmaceutical research studies involving outpatient oral medications to validate patient compliance with the research protocols.

The dispenser comprises identification security features, programmability, a memory component for storing prescribed and actual dispensing episodes and the ability to report dispensing episodes to a remote monitoring site.

Since the A-MOD dispenser is portable, its use to dispense medications between clinic visits by the patient solves a patient travel problem. Also, compliance with the prescribed dosing schedule is monitored as the patient must demonstrate compliance by reporting to the monitoring clinic (e.g., a remote monitoring site) through an internet site or by sending an over-the-air signal to the monitoring site. The A-MOD dispenser reports the collected dispensing information (e.g., days and time of days administered) on a daily basis, for example, or a more or less frequent interval. To meet the reporting compliance requirement, the device must remain intact and functional. The A-MOD dispenser must therefore be constructed to resist tampering and unauthorized removal of the medications.

The A-MOD device with its identification security, programmability, memory of dispensing episodes and remote reporting capability may ultimately be used in numerous applications while discouraging diversion, accidental overdosing and mistaken use of high risk medications. Although initially intended for use with substance abuse patients, it is anticipated that the A-MOD dispenser may be used in numerous other applications where these features are important. Substance abuse patients will appreciate the safe, secure, and remote medication dispensing offered by the A-MOD dispenser. Also, the A-MOD dispenser's modular components can be modified as needed to serve other patient groups who may benefit from its use.

The A-MOD dispenser not only supplies a patient's medications and enforces compliance with a dosing plan, it also stores the date and time-of-day when the medication was requested. Presumably the medication dose has been removed from the dispenser and self-administered by the patient shortly after requested. Other collected and stored timing parameters include, but are not limited to, time of a first dispense, an interval between dispensing consecutive medications, the amount of time to wait for a patient/user to begin the authentication process after the interval between doses has elapsed, timeouts and hold-offs associated with attempted unauthorized access. Generally, as used herein the words "dispensed," "dispense," and "dispensing times" refer to that time when the patient has requested a medication dose by executing an authentication procedure as described elsewhere herein, It is assumed the time at which the patient administers the dose occurs within minutes of a successful authentication. If the patient is receiving pain medications from the dispenser the patient would not execute the authentication process if he/she did not want to take the next pain medication dose, that is, the patient's pain is not at a level that warrants taking a pain-reducing medication.

Typically, the time the medication is requested is nearly the same as the time when the medication is removed from the dispenser and taken by the patient. Thus according to this embodiment the request time is stored, recognizing that the time the dose is removed is nearly concurrent with the request time and the administration time. In another embodiment having a sensor proximate a medication access opening, the sensor can supply a time when the medication dose was removed from the dispenser. Thus in this later embodiment both the request time and the removal time are determined and recorded.

In an embodiment having a motor to drive a belt carrying the medication doses in medication compartments, after the user removes a dose the motor is activated to move the belt, but the belt stops halfway to the next dose compartment. Thus the user cannot gain access to the next dose until the minimum dosing interval has elapsed and he/she is again authenticated. In another embodiment after the user removes a dose, the belt does not move but remains in position until the patient authenticates again to the dispenser.

In an embodiment having manual belt control, after the user is authenticated, she/he manually moves the belt to place the next dose in position for dispensing. Once a dose is moved into position at the dose opening or portal, it remains in that position until administered by the patient/user. For controlled substances, such as opioids, the patient/user is instructed not to undertake the authentication process until he/she wants to take a dose. If the patient/user is successfully authenticated, but does not administer a dose, an unauthorized third party can remove the controlled substance does from the dispenser. This is a situation to be avoided. After the dose has been moved into position at the portal, the belt cannot be moved until the next dosing time arrives and the user is authenticated.

In the various A-MOD embodiments the data related to the actual dosing times (referred to as actual medication dispensing information) can be downloaded from the A-MOD device to a computer platform via a USB port on the A-MOD device, over a wired link or via a wireless connection (using a transmitter and receiver disposed within the A-MOD dispenser), such as a mobile telephone link. The patient user can also access, via the Internet, his/her virtual clinic (also referred to as a remote monitoring site or website) to download the actual medication dispensing information to the monitoring site. This actual medication dispensing information can be used to prove compliance with the prescribed dosing regimen. The computer platform can also upload the prescribed medication dispensing information from the monitoring website and further upload the prescribed dispensing information to the A-MOD dispenser.

According to other embodiments, the A-MOD device is directly linked to the remote monitoring site for downloading the actual medication dispensing information and for receiving programming information. Access to an internet site is not required for this embodiment.

Any embodiment with remote connection features may especially benefit rural patients or those unable to secure transportation to a clinic multiple times each week.

Various embodiments of the A-MOD incorporate remote wireless connection technologies such as WiFi, Bluetooth, near-field communications and/or far-field communications and wired remote communications techniques such as Ethernet and dial-up modems.

Secure communications protocols can be used to avoid spoofing of the communications protocol. These include SSL (secure sockets layer) or other types of secure or encrypted communications mechanisms.

The A-MOD dispenser is a secure portable medication dispensing device that ensures compliance with medication dosing regimens while preventing diversion and inadvertent drug overdosing. The A-MOD device has two principal components. (1) an electronic component (also referred to as an A electronic component or module) that is programmed (for example, from a computer via a USB port on both the A-MOD and computer or via a communications port on both the A-MOD and the computer) to permit authenticated user access to a medication dose at pre-designated times or at a specified time interval between doses. The A electronic component also comprises the various electronic devices/components imparting functionality to the A-MOD dispenser. (2) A medication component (also referred to as an M medication component or module) containing a disposable or refillable medication cassette. In one embodiment the cassette comprises a continuous belt having a plurality of medication-carrying compartments defined in an exterior-facing surface of the belt.

The two components are locked together using a proprietary tool. When locked the two modules function as a single device, i.e., the A-MOD dispenser. The locking mechanism may comprise an electronic or magnetic system or a mechanical system (e.g., an electro-mechanical lock or keyed lock) that prevents easy separation of the components without a specific electronic command or special tool. In one embodiment tampering with the locking mechanism triggers an alarm.

Permitting separation of the two components provides flexibility in mating different functional components to the A electronic component or the M medication component. For example, separating the A and M components allows refilling the medication slots or compartments in the M component at a pharmacy without requiring the A electronic component. This feature also allows pre-packaging of medication slots of the M component for later insertion into the M component and attachment of the M component to the A electronic component.

The A-MOD uses its USB or wireless connection port to connect to a computing platform for programming the device and for transferring the collected data into to the computing platform. This can be accomplished with a connecting conductor between the A-MOD and the computing platform or over a wireless link. The computing platform can then be connected to an internet-based "virtual clinic" to download the A-MOD medication administration data (i.e., actual medication dispensing information) to show dosing compliance with the prescribed dosing schedule, to receive patient messages from the virtual clinic and to allow patient participation in online educational and counseling seminars. In one embodiment, during the online educational or counseling seminars, the user is requested to authenticate himself/herself to ensure that the person participating in the seminar is the assigned user of the A-MOD device.

The A-MOD dispenser can be used by patients in drug abuse clinics to reduce the need for patient travel to the clinic and also to enable patients to be closely monitored from the "virtual clinic," as the patient achieves their outpatient medication goals. However use of the A-MOD dispenser is not limited to this application.

Figure 1:
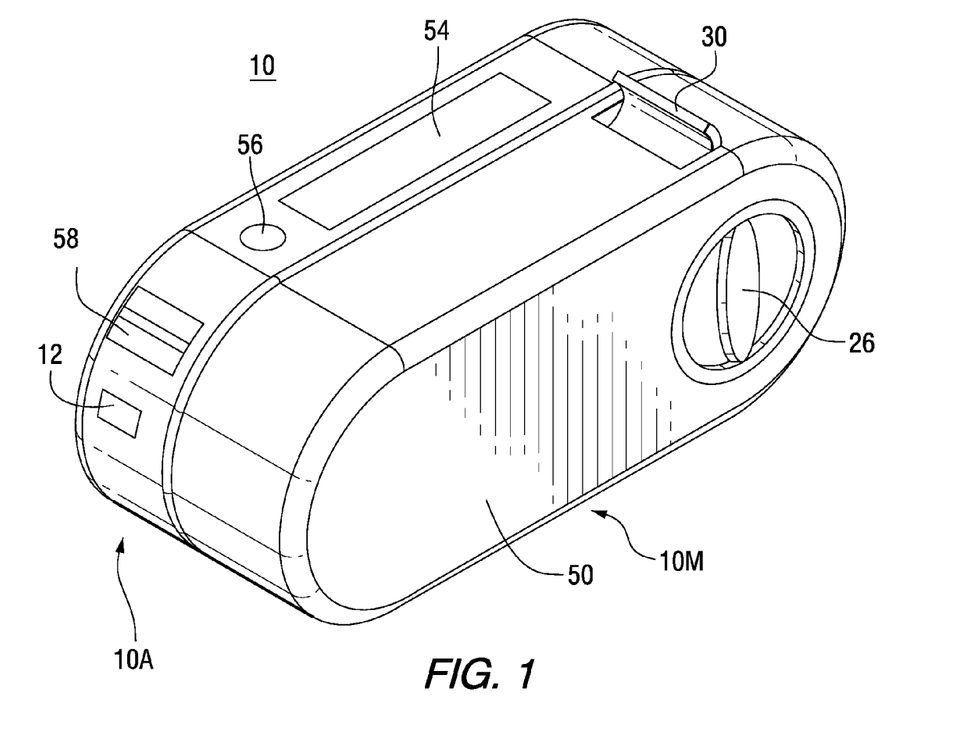
FIG. 1 is perspective view of an ambulatory medication-on-demand dispenser according to the teachings of the present invention.

FIG. 1 illustrates one embodiment of the A-MOD dispenser 10. In one embodiment the A-MOD dispenser 10 is nominally about 5 cm×12 cm×3 cm. Given its small size, the dispenser can be carried in a purse, briefcase or pocket. Advantageously, an A electronic component 10A can be separated from an M medication component 10M for loading new medications, for example; otherwise the components 10A and 10M are securely locked together.

Within the M medication component 10M medications are carried in a series of medication compartments, slots or wells 20 (thirty compartments in an exemplary embodiment) formed in a movable track or belt 22. See cutaway views of FIGS. 2, 3, 4 and 5. Exemplary medication slots 20 are illustrated, although these slots can be enlarged or reduced in size or changed in shape to accommodate differently sized and shaped medications. The belt 22 is movable by user operation of a knob 26 (see FIG. 1) extending through an outside surface of the dispenser 10. As the belt 22 moves, each slot 20 passes a pill door, opening, or access portal 30 for patient removal of the medication dose 34. As discussed above, in another embodiment the A-MOD dispenser comprises a motor for moving the belt 22.

According to one embodiment, the complete M medication component 10M, including the medication slots 20 disposed therein, is disposable. In another embodiment the belt 22 and the medication slots 20 are removable from the M medication component 10M and separately disposable or refillable.

According to one embodiment, the medication slots 20 are formed in an external-facing surface of the pliable/flexible belt 22. The belt 22 is mounted on two spindles 40 and 41 spaced apart along the major axis of the ellipse. See FIG. 5. One of the spindles 40 or 41 is attached to the knob 26 (see FIG. 1) so that manual rotation of the knob 26 causes the attached spindle 40 or 41 to rotate, thereby driving the belt 22 and the medication compartments 20 formed therein. The non-driven spindle is free-wheeling.

Figure 5:
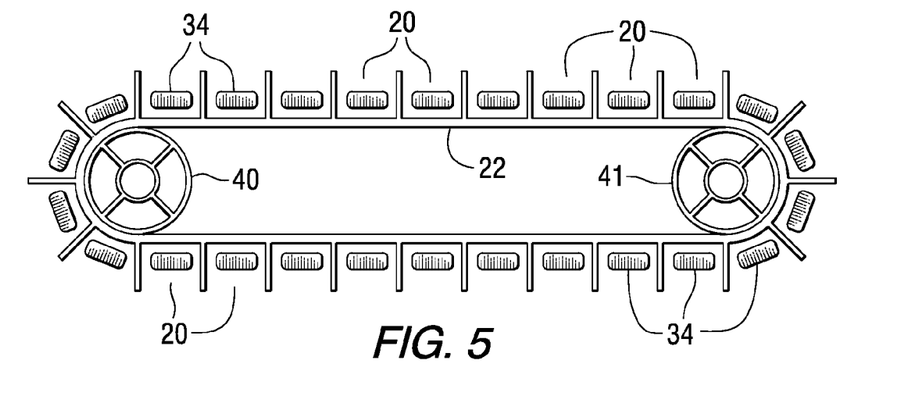
FIG. 5 illustrates a track, for carrying medication doses, disposed internal to the ambulatory medication-on-demand dispenser of the present invention.

A FIG. 5 embodiment illustrates the belt 22 moved by rotation of one of the spindles 40 or 41. The spindles are turned by operation of the knob 26 described above and illustrated in FIG. 1. An inner surface of the belt 22 may be notched to increase friction between the track's inner surface and an outer circumferential surface of the spindles 40 or 41. The FIG. 5 elements are enclosed within an outer housing 50 of the M medication compartment 10M to retain the doses within the slots 20 until dispensed to the user.

Using a suitable dose carrier, a pharmacy can fill the slots 20 and insert the track/slots into the outer housing 50. After mating the track/slots with the outer housing 50, a label 54 identifying the medication doses and the patient is affixed to an outside surface of the outer housing 50 as illustrated in FIG. 1.

Generally, a surface of the M medication component 10M opposite from the knob 26 includes both a mechanical and electrical connector for connection to the A electronic component 10A. When the M medication component 10M is connected to the A electronic component 10A, the angle through which the knob 26 can be turned is either mechanically or electrically prevented until a successful authentication has been made.

Illumination of a light emitting diode (LED) 56 indicates that the next medication dose can be administered, i.e., the minimum dosing interval has elapsed or the time for administering the next dose has arrived. In lieu of or in addition to illuminating the LED 56, an audible alarm can be activated, and/or alerts can be sent to the user's (or family member's) mobile phones.

The user/patient must first be authenticated as the user to whom the A-MOD has been assigned. The authentication process is executed when the user passes a finger tip across a finger print sensor 58 in FIG. 1. After successful authentication, the user/patient can manually turn the knob 26 and dispense the next medication dose through the opening 30. Or in another embodiment the belt is automatically moved to present the next medication dose at the opening. Typically, the user/patient would not undertake the authentication process unless he/she desires or needs a medication dose. For example, if the medication dose comprises a pain medication, the user/patient undertakes the authentication process only if the pain is sufficiently severe to warrant the administration of a pain medication. Of course, the authentication procedure is active only after the minimum dosing interval has elapsed. If the user/patient is not experiencing pain when the minimum dosing interval has elapsed, she/he will not want a pain medication and would therefore not execute the authentication procedure. However, the patient can execute the authentication procedure later when his/her pain has returned and he/she desires to take a medication dose.

The fingerprint authentication technique provides dispenser security by requiring user fingerprint identification at the finger print sensor 58 illustrated in FIG. 1. However, it is necessary for the patient/user to pre-register his/her fingerprint in the dispenser 10 for later use to authenticate the patient/user. Other authentication devices, and associated sensor and control features, such as a bar code worn by the user (on a bracelet, for example), a retinal scan and a voice scan, for example, can be used in lieu of the fingerprint identification device.

Storing the assigned user's fingerprint can be accomplished as part of the A-MOD configuration process when the A-MOD is first assigned to the user. Alternatively, this process can be carried out during a "first use" of the A-MOD dispenser.

The dispenser can be programmed with a real clock-time of the medication dosing or programmed to provide the medication on an as-needed basis with a required number of hours between successive doses (the latter referred to in the medical community as prn dosing). Programming is accomplished by docking the dispenser's A electronic component 10A via a USB or wireless connection port 12 to a computing platform (not shown) also having a USB access port or a wireless connection port. The computing platform includes appropriate programming software for programming the dispenser.

Contents of the dispenser memory (i.e., dates and times of actual and prescribed medication administration) can be uploaded from the dispenser memory to the computing platform through the USB or wireless connection port 12, and from the computing platform to a patient monitoring clinic. Typically, the clinic provides an internet site to which the dosing information is uploaded. Thus the communications link connecting the dispenser 10, the computing platform and the internet site can enable remote monitoring, remote dispensing overrides, data collection and data recording. Another embodiment comprises wireless or cellular communication components for use in lieu of accessing the remote site through the Internet.

The patient is alerted that a medication dose is available (i.e., the prn interval has elapsed) and may be self-administered by illumination of the LED 56 of FIG. 1. After observing the illuminated LED, but not before, to obtain the medication dose the patient touches the fingerprint sensor 58 and if recognized as the authorized patient the knob 26 is unlocked. The patient manually turns the knob 26 to move a single medication dose into alignment with the dose access portal 30. See FIG. 1. The knob 26 is configured to allow only the next dose to be moved into alignment with the access portal 30; the knob cannot be turned continuously.

Figure 2:
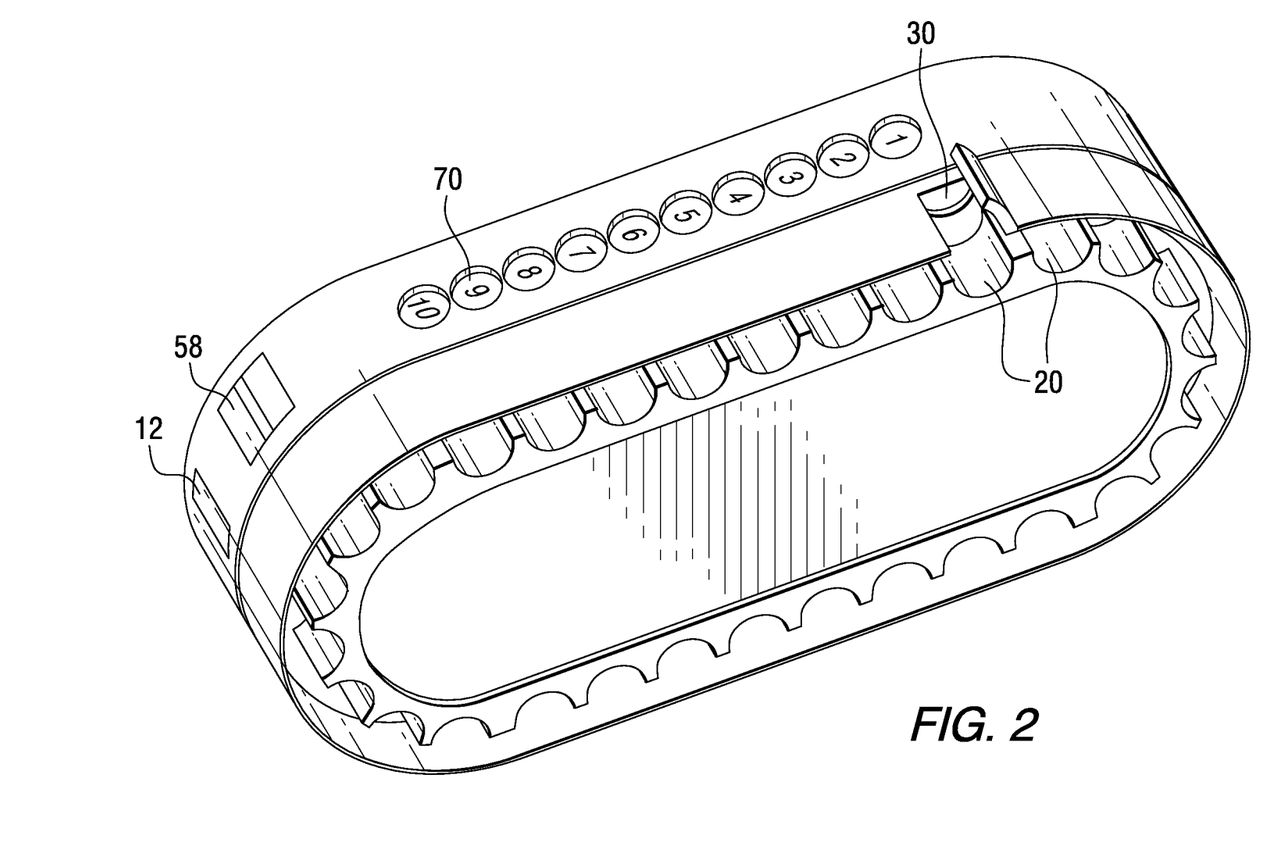
FIGS. 2-4 are additional cut-away perspective views of the ambulatory medication-on-demand dispenser of the present invention.
Figure 3:
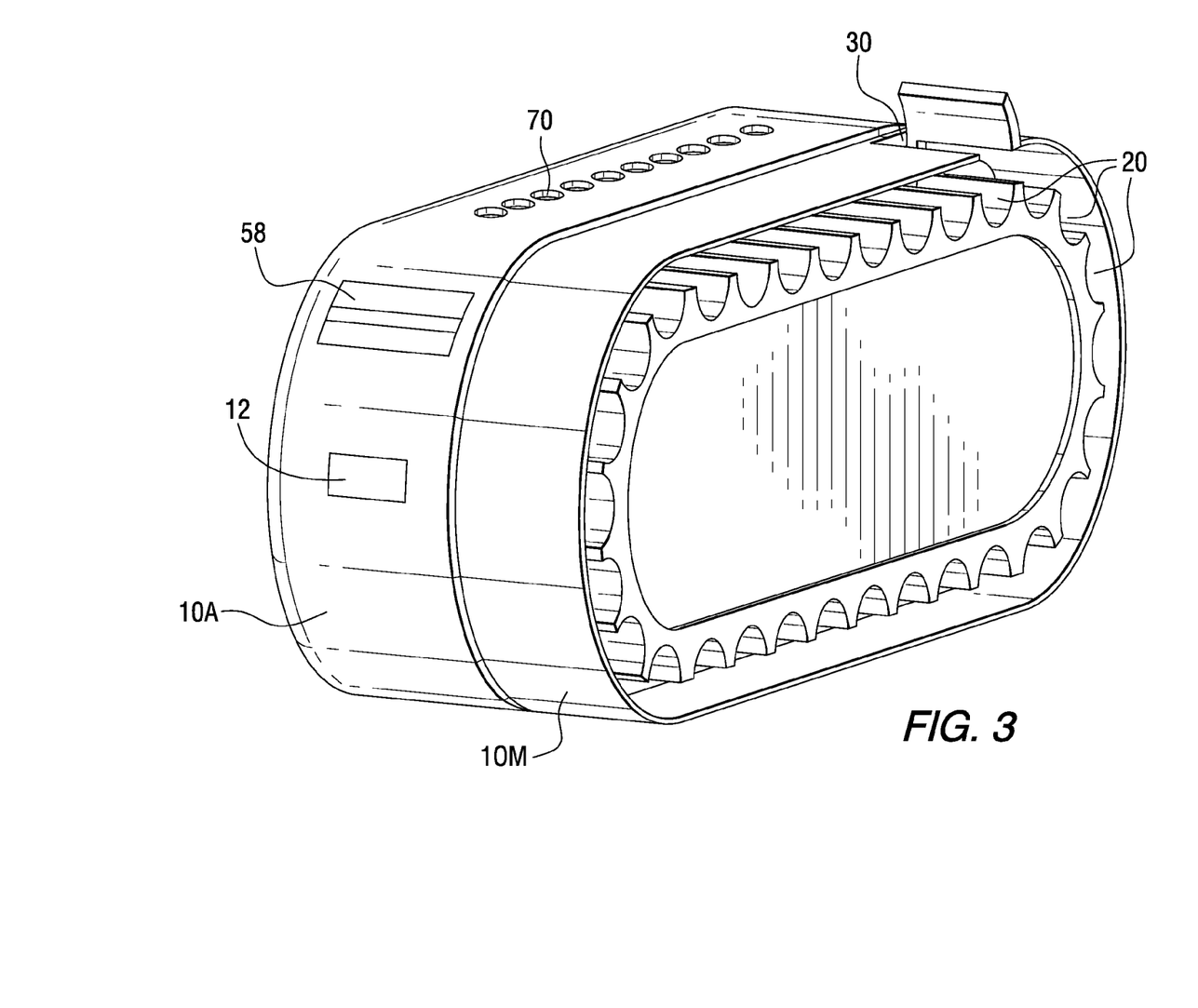
Figure 4:
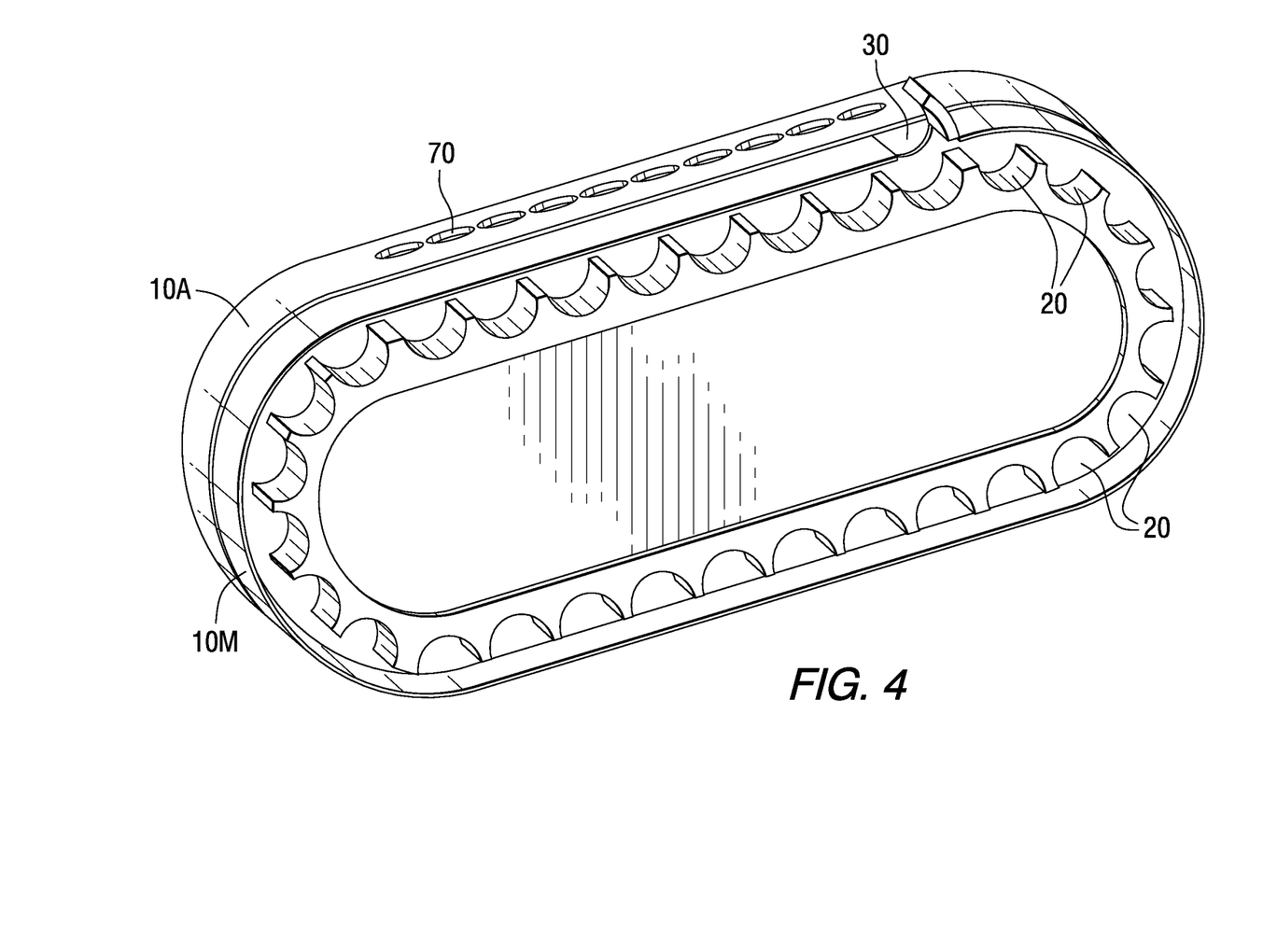

When administering a medication dose for pain control, the patient uses a pain scale 70 of FIG. 2 to enter a numerical value indicative of the patient's present pain. According to one embodiment the patient is required to enter the pain score after authentication before the knob 26 can be turned to dispense a medication dose. In applications where the A-MOD is not used to control pain, the illustrated pain scale is not required.

Once access is granted, the patient can turn knob 26, and the medication dose is accessible through the portal 30, access will not be granted again until the LED 56 is illuminated as per the preprogrammed prescribed dosing schedule. The A-MOD 10 dispenser stores the date and time of the fingerprint authentication or the date and time when the knob 26 is released (note these two times should be nearly coincident.)

Compliance with dispenser use is mandated by requiring return of the A-MOD dispenser 10 to a clinic for a medication refill. In particular, substance abuse clinics or pain clinics may supply the medication refills, requiring the patient to return the empty device to clinic. The empty M medication component 10M is separated from A electronic component 10A, using the described unlocking mechanism. A filled M medication component 10M is attached to the A electronic component 10A and the latter reprogrammed as required. The entire A-MOD device 10 is then returned to the patient.

In one application, the dispenser 10 must be retained intact to register into the "virtual clinic" at regular intervals for outpatient follow-up. This scenario requires a tamper resistant feature to permit detection of any attempts to tamper with or damage the A electronic component 10A or the M medication component 10M, or gain access to the medication doses in the M medication component 10M. Broadly, the tamper resistant feature is embodied within the latching, dispensing and authentication processes of the A-MOD dispenser. Any tamper attempt may prevent proper operation of the A-MOD dispenser 10.

The A electronic component 10A is an electromechanical component that controls medication dispensing and includes software that enables dispenser programming and operation. The electronic compartment 10A also includes the dispenser memory and electronic components for interfacing with the computer, in an application where the computer is used, to report the patient's actual dispensing times.

In one embodiment the A electronic compartment 10A further comprises the fingerprint sensor 56 and associated electronics, the LED 56, a microprocessor (not shown) for controlling the dispenser 10, the USB/wireless port 12, and connectors for receiving battery power to power the dispenser 10. The fingerprint sensor 56 and associated electronics enforce access control/authentication as described above. A small low power microprocessor contains the dispensing parameters and generates a signal to release a lock that then permits manually turning of the knob 26. In an embodiment having a motor to control the belt of the A-MOD dispenser, the signal activates the motor for turning the medication slots 20 to position the next slot at the access portal 30.

The fingerprint sensor 58 interacts with software components of the A-MOD dispenser 10. In one embodiment the fingerprint sensor 56 comprises a slot-type sensor that reads the fingerprint as it is passed over a small slot within the sensor. Once read, the fingerprint is analyzed for key attributes that are compared with an attribute list previously stored in the A-MOD dispenser 10, specifically within the memory and/or the microprocessor. Only after proper authentication is the knob lock released for manual turning to present the next dose at the access portal 30.

The software component of the A-MOD dispenser 10 and its supporting software architecture comprises at least three separate applications:
controlling the dispenser's mechanical components;
programming the device for dispensing according to the prescribed dosing parameter; and
recording times of medication dispensing for reporting to the remote monitoring site either directly or via the computing platform.

Thus the software controls the A-MOD dispenser and provides data communications mechanisms for programming, logging, and tracking. Certain of these applications reside in the A-MOD dispenser, while others reside on the host computer that is linked to the A-MOD dispenser or at the remote monitoring site. The A-MOD software application controls programming and implements the access compliance function (fingerprint reading or sensing another biometric characteristic) and controls the electro-mechanical components for dispensing medications. The dispenser application also includes software elements that log all activity and attempts to dispense medications and transfers this information to the host computer for transfer to the monitoring site or transfers the information directly to the remote monitoring site.

One of the software applications requires a graphical user interface (GUI) that allows programming of the A-MOD dispenser with appropriate dispense intervals and access/authentication parameters. Access/authentication parameters may include whether a fingerprint is required and if so, a fingerprint scan from one or more patient fingers.

According to one embodiment, the programming interface requires connecting the host computer or the monitoring site to the A-MOD dispenser via the dispenser USB/wireless connector port. The software program that executes the dispenser functions is displayed on the host computer. A simple programming screen appears for the user to enter the medication name, dose and times of dosing or the minimal required time interval between doses. In another embodiment the information is entered by selecting from a pull down menu. Once the information is entered, a confirmation screen appears and prompts the user to confirm that the entered information is correct. If not correct the program returns to the entry screen. Once the information is correct and confirmed, the user exits the program and removes the USB connector or terminates the wireless link.

Another software application resident on the computing platform that interacts with the A electronic unit 10A stores and controls actual dosing information and transferring this information to the remote monitoring site (clinic, hospital, etc).

Generally, the software applications resident on the computing platform interact with corresponding software applications stored within the A electronic unit 10A of the A-MOD dispenser.

In one embodiment, electronic data stored in the dispenser and transmitted to the monitoring site is encoded or otherwise encrypted during transmission.

Given the portable nature of the A-MOD dispenser, power is supplied from a replaceable battery or a rechargeable battery that can be recharged in a cradle plugged into an AC power source or via a physical USB port from a computer. These elements are not shown in the Figures. The A-MOD dispenser can also receive power from a conventional wall outlet power source when its portability feature is not required.

Figure 6:
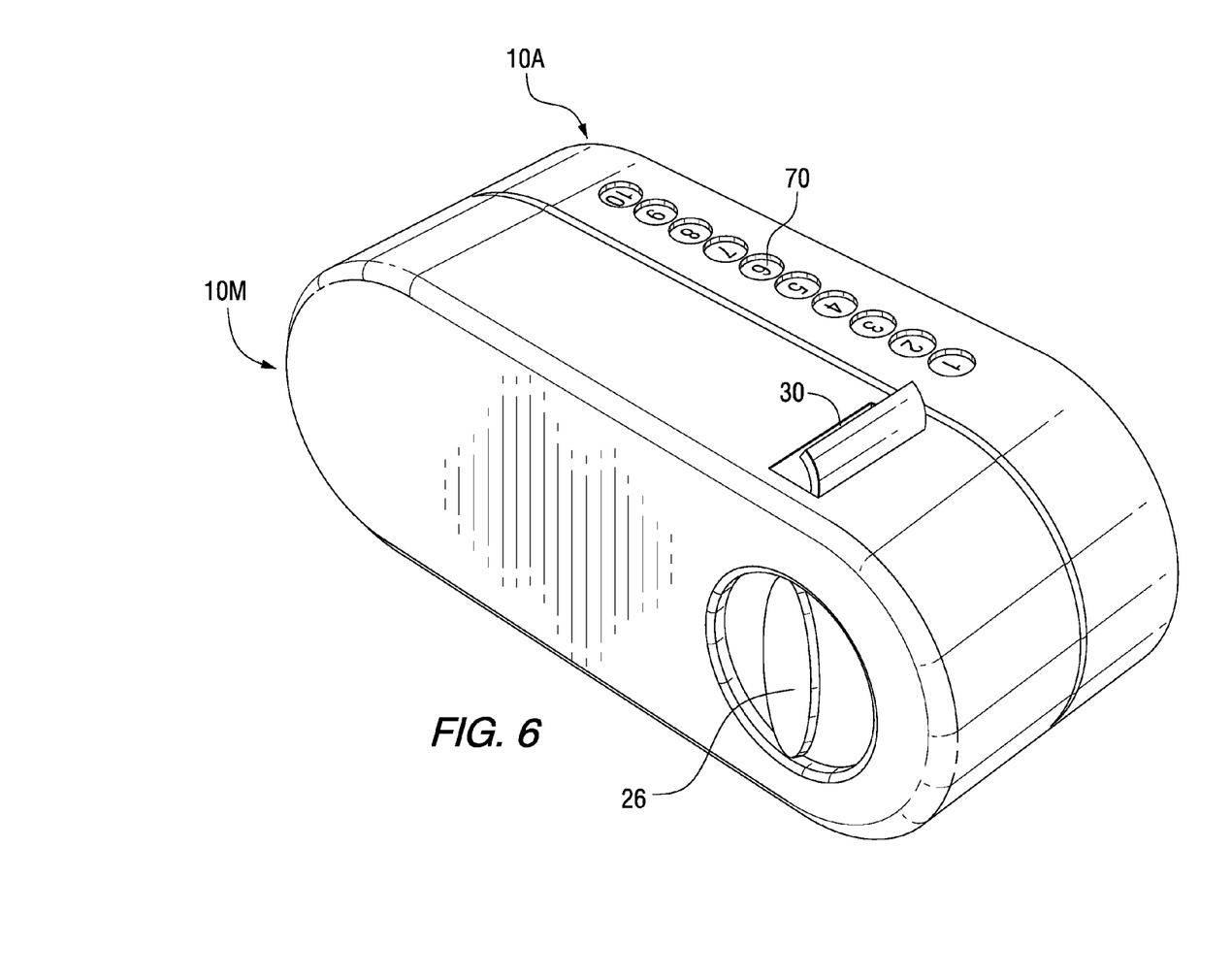
FIG. 6 is an additional perspective view of the ambulatory medication-on-demand dispenser of the present invention.

FIG. 6 illustrates a perspective view of the A-MOD dispenser 10, including various elements of the A-MOD dispenser described above.

Figure 7:
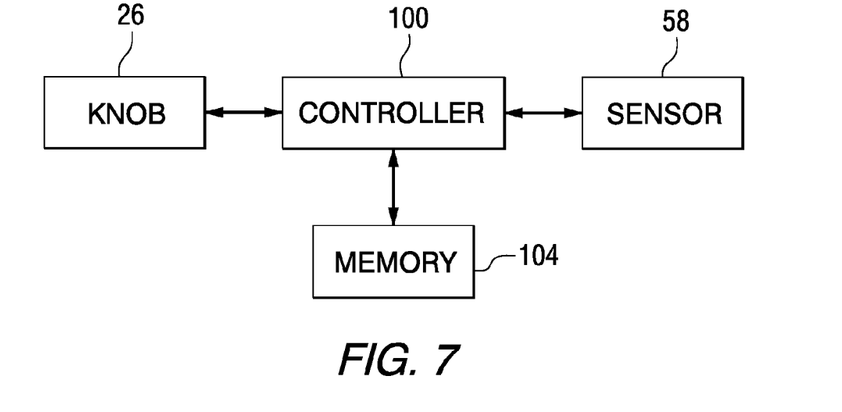
FIG. 7 is a block diagram depicting the functional blocks and interconnections of the present invention.

FIG. 7 illustrates a block diagram of the principal functional blocks of the present invention. A controller 100 controls overall operation of the A-MOD dispenser 10, including releasing the knob 26 for manual rotation by the user, activating the LED 56 at appropriate times, and comparing the biometric information provided by the user (for example, a fingerprint at the fingerprint reader 58) with biometric information of the authorized users stored in a memory 104.

Generally, features of the A-MOD dispenser comprise secure dispensing in a portable oral dispenser, limited access to only authenticated users/patients, accommodating prn dosing regimens, data transfer from the dispenser to a remote monitoring site, and separation of the dispenser into two components, only one of which carries the medication doses.

Other known medication dispensers including those having a patient authentication feature dispense according to a fixed time interval between doses, and therefore the timing of each dose is controlled by clock time, e.g., every 8 hours. The present invention differs from these known dispensers since it dispenses on a variable time interval (but with at least a minimum time interval) that is measured from the user's most recent successful authentication to the dispenser (which is assumed to be nearly concurrent with the time when the patient had administered a dose). Thus the present invention implements a prn dosing regimen whereas the prior art dispensers implement a time-scheduled or time-based dosing regimen.

Notwithstanding its intended use on a prn dosing interval, the A-MOD dispenser can also be used to dispense psychogenic patient medications that must be taken on a periodic basis. In this application the A-MOD dispenser, by tracking dosing intervals, mandates compliance with the dosing regimen of these medications. If a psychiatric patient is not compliant he can relapse, which may require hospitalization or result in adverse behavioral events. By remote monitoring the A-MOD dispensing times for compliance, if non-compliance is determined the patient can be contacted and restarted on medication or hospitalized to mandate compliance.

Pain medications are frequently prescribed on a prn basis. If the medication is taken more frequently than the prescribed prn interval the patient may suffer adverse health effects. If these medications are delivered by a dispenser of the present invention and the patient is not suffering pain and does not need or want a pain medication, the dispenser can accommodate this situation. If the patient is not in pain, the patient simply does not begin the authentication procedure once alerted that the prn minimum dosing interval has elapsed. But once the prn interval has elapsed, at any future time when the patient needs a pain medication he can provide the biometric information to be authenticated to the dispenser and if successfully authenticated or authorized the dispenser will make a medication dose available. Thus anytime after the prn interval has elapsed, when the patient desires a medication dose (to control pain for example) the patient can provide biometric information, be authenticated to the dispenser and receive a medication dose.

The feature that permits the patient to authenticate and take the dose anytime after the prn interval has elapsed (i.e., without a time limit) is comforting to the patient since he will not worry that the A-MOD will later "time out" and thus the dose will not be available. This is reassuring to the patient and allows her to comfortably wait until she really needs the medication to take it. Generally this feature is incorporated into the A-MOD when the dispenser is used to track the use of the pain medications. But this feature would not be incorporated in an A-MOD dispenser embodiment that is used to determine patient compliance with a dosing schedule, that is, when the dose must be taken at designated time intervals, such as for use with psychiatric patients as described above.

The design and operation of the A-MOD also ensures against diversion of controlled substances, especially pain medications and opioids.

Note that the above discussion describes at least two different applications for the A-MOD dispenser. In a first application the patient/user is dispensed medication doses on a predetermined dosing schedule and the dispenser monitors compliance with that schedule. A psychiatric patient receiving psychotropic drugs is one example of such a user/patient. In a second application the patient/user is dispensed medication doses on a prn dosing schedule and the dispenser ensures that the next dose is not available until the prn interval has elapsed and the dose is available any time after the prn dosing interval has elapsed. Pain medications are commonly dispensed on this basis.

In the first application the LED 56 serves as a reminder to the patient/user to take the medication. In the second application the LED 56 advises the patient/user that the next dose can be taken now or later when it is needed, as the minimum dosing interval has elapsed.

Although the invention has been shown and described with respect to a certain preferred embodiment or embodiments, equivalent alterations and modifications may occur to others skilled in the art upon the reading and understanding of this specification and the annexed drawings. In particular regard to the various functions performed by the above described components (assemblies, devices, circuits, etc.), the terms used to describe such components are intended to correspond, unless otherwise indicated, to any component that performs the specified function of the described component (i.e., that is functionally equivalent), even though not structurally equivalent to the disclosed structure, which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A medication dispenser for dispensing medications on a prn as-needed basis, the medication dispenser comprising:
    a sensor for receiving biometric information from a user;
    a memory device for storing a prescribed minimum dosing interval between successive medication doses;
    a belt and a plurality of medication-carrying slots on an exterior-facing surface of the belt;
    a dose opening defined in an exterior surface of the medication dispenser;
    a signaling device;
    when the prescribed minimum dosing interval has elapsed, a controller for activating the signaling device and the sensor to an active state, the signaling device in the active state for advising the user the minimum dosing interval has elapsed, the sensor in the active state for receiving biometric information from the user, the signaling device and the sensor remaining in the active state until at least the user has been determined to be an authorized user;
    the controller further responsive to the biometric information for determining whether the user is an authorized user;
    upon determining the user to be an authorized user, the controller further for controlling the belt to allow manual or automatic movement of the belt to align a medication-carrying slot with the dose opening, the medication-carrying slot remaining aligned with the dose opening until withdrawn by the user; and
    to determine whether the prescribed minimum dosing interval has elapsed, the controller further for comparing the prescribed minimum dosing interval with a time interval beginning at an immediately prior withdrawal of a dose from the dose opening and ending at a later time when an authorized user needs a dose and therefore withdraws a dose from the dose opening, the interval between successive doses thus comprising an interval of variable length as dependent on an authorized user's need for a dose, the interval between successive doses thus not having a fixed or a predetermined length.

2. The medication dispenser of claim 1 wherein the controller automatically controls movement of the belt by activating a motor to move the belt to present a medication within a medication-carrying slot at the dose opening.

3. The medication dispenser of claim 1 wherein the controller controls the belt by permitting manual movement of the belt by the user, the manual movement to present a medication within a medication-carrying slot at the dose opening.

4. The medication dispenser of claim 1 wherein the sensor comprises one of a fingerprint sensor, a voice sensor, and a retinal sensor.

5. The medication dispenser of claim 1 comprising an A electronic component further comprising the sensor, the controller, and the memory component, and comprising an M medication component further comprising the continuous belt and the dose opening.

6. The medication dispenser of claim 1 wherein the memory device stores actual medication dispensing information further comprising one of a time and a date when the dose is presented to the user at the dose opening, and a time when the user is determined to be an authorized user.

7. The medication dispenser of claim 1 further comprising a communications device that communicates with a monitoring site via one of an over-the-air transmission path, a public-switched telephone network or an Internet.

8. The medication dispenser of claim 7 wherein the monitoring site provides the prescribed minimum dosing interval to the medication dispenser for storing in the memory device.

9. The medication dispenser of claim 7 wherein the communications device comprises a bi-directional communications device for communicating actual medication dispensing information to the monitoring site and receiving prescribed medication dispensing information from the monitoring site.

10. The medication dispenser of claim 1 further comprising a first and a second spaced-apart spindle and the belt is disposed to span a distance between the first and second spindles.

11. The medication dispenser of claim 10 further comprising a knob connected to one of the first and the second spindles, wherein rotation of the knob causes movement of the belt and the medication slots such that a medication dose is presented at the dose opening, wherein the user can manually rotate the knob after the controller determines the user is an authorized user.

12. The medication dispenser of claim 1 wherein at any time after the controller has activated the signaling device and the sensor to the active state, the user can provide biometric information for determining whether the user is an authorized user.

13. A medication dispenser for dispensing medications on a prn as-needed basis, the medication dispenser comprising:
   a medication component for carrying medication doses within slots formed in a movable belt spanning a distance between a first and a second spindle, the belt movable to present a medication dose at a dose opening defined in a housing of the medication component;
   a biometric sensor for receiving biometric information from the user;
   a signaling device;
   an electronic component comprising a controller for unlocking the belt to permit manual operation of the belt by the user to align a medication-carrying slot with the dose opening;
   if the prescribed minimum dosing interval has elapsed, the controller for activating the signaling device and the sensor to an active state, the signaling device in the active state for alerting the user the minimum dosing interval has elapsed, the sensor in the active state for receiving biometric information from the user, the signaling device and the sensor remaining in the active state until the user has been determined to be an authorized user;
   the controller further responsive to the biometric information for determining whether the user is an authorized user;
   upon determining the user to be an authorized user, the controller further for unlocking the belt to allow manual movement of the belt to align a medication-carrying slot with the dose opening, the medication-carrying slot remaining aligned with the dose opening until withdrawn by the user; and
   to determine whether the prescribed minimum dosing interval has elapsed, the controller further for comparing the prescribed minimum dosing interval with a time interval beginning at an immediately prior withdrawal of a dose from the dose opening and ending at a later time when an authorized user needs a dose and therefore withdraws a dose from the dose opening, the interval between successive doses thus comprising an interval of variable length as dependent on an authorized user's need for a dose, the interval between successive doses thus not having a fixed or a predetermined length.

14. A method for dispensing a medication dose prescribed on a prn as-needed basis, the method comprising:
   storing a prescribed minimum dosing interval between successive medication doses;
   activating to an active state a signaling device and a biometric sensor only when the prescribed minimum dosing interval has elapsed, the signaling device and the sensor remaining in the active state until the user has been determined to be an authorized user;
   the sensor for receiving biometric information from the user any time after activation of the signaling device and the sensor, but not before activating the signaling device and the sensor;
   responsive to the biometric information, authenticating the user as an authorized user of a medication dispenser;
   upon determining the user to be an authorized user, controlling a continuous belt having a plurality of medication-carrying slots defined on an exterior-facing surface of the belt to present a medication dose at a dose opening defined in an exterior surface of the medication dispenser, the medication dose remaining at the dose opening until withdrawn by the user;
   for determining whether the prescribed minimum dosing interval has elapsed, comparing the prescribed minimum dosing interval with a time interval beginning at an immediately prior withdrawal of a dose from the dose opening and ending at a later time when an authorized user needs a dose and therefore withdraws a dose from the dose opening, the interval between successive doses thus comprising an interval of variable length as dependent on an authorized user's need for a dose, the interval between successive doses thus not having a fixed or a predetermined length; and
   redetermining when the next minimum dosing interval will elapse after each successful authentication of the user.

* * * * *